(12) United States Patent
Hasko

(10) Patent No.: US 10,806,747 B2
(45) Date of Patent: Oct. 20, 2020

(54) METHODS FOR TREATING INFECTION INCLUDING SEPSIS VIA P2X RECEPTOR MODULATION

(71) Applicant: Rutgers, The State University of New Jersey, New Brunswick, NJ (US)

(72) Inventor: Gyorgy Hasko, Gillette, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 16/034,789

(22) Filed: Jul. 13, 2018

(65) Prior Publication Data

US 2019/0015438 A1  Jan. 17, 2019

Related U.S. Application Data

(60) Provisional application No. 62/532,619, filed on Jul. 14, 2017, provisional application No. 62/562,770, filed on Sep. 25, 2017.

(51) Int. Cl.
| | | |
|---|---|---|
| *A61K 31/70* | (2006.01) | |
| *A01N 43/04* | (2006.01) | |
| *A61K 31/7076* | (2006.01) | |
| *A61P 31/04* | (2006.01) | |
| *A61K 31/366* | (2006.01) | |
| *A61K 31/7048* | (2006.01) | |

(52) U.S. Cl.
CPC ........ *A61K 31/7076* (2013.01); *A61K 31/366* (2013.01); *A61K 31/7048* (2013.01); *A61P 31/04* (2018.01)

(58) Field of Classification Search
None
See application file for complete search history.

(56) References Cited

PUBLICATIONS

Hutson et al. Transplant Infectious Disease (2009), vol. 11, pp. 277-280.*
Csoka et al. The FASEB Journal (2015), vol. 29, No. 9, pp. 3626-3637.*
Pettengill, Matthew A., et al. "Ivermectin inhibits growth of Chlamydia trachomatis in epithelial cells." PLoS One 7.10 (2012).*
Izquierdo, Isabel, et al. "Fatal strongyloides hyperinfection complicating a gram-negative sepsis after allogeneic stem cell transplantation: a case report and review of the literature." Case reports in hematology 2013 (2013).*
Lichtenberger et al. Transplant Infectious Disease (2008), vol. 11, pp. 137-142.*
Salluh, J. I. F., Feres, G. A., Velasco, E., Holanda, G. S., Toscano, L., & Soares, M. (2005). Successful use of parenteral ivermectin in an immunosuppressed patient with disseminated strongyloidiasis and septic shock. Intensive care medicine, 31(9), 1292-1292.*
Mejia et al. Curr Opin Infect Dis. (2012), vol. 25(4), pp. 458-463.*
Stokes et al. "P2X4 receptor function in the nervous system and current breakthroughs in pharmacology." Frontiers in pharmacology 8 (2017): 291.*
Antonioli et al. "CD39 and CD73 in immunity and inflammation" Trends Mol Med 2013 19:355-367.
Benjamim et al. "The chronic consequences of severe sepsis" J Leukoc Biol 2004 75:408-412.
Burnstock, G. "Pathophysiology and therapeutic potential of purinergic signaling" Pharmacological Reviews 2006 58:58-86.
Coutinho-Silva et al. "Modulation of P2Z/P2X(7) receptor activity in macrophages infected with Chlamydia psittaci" Am J Physiol Cell Physiol 2001 280:C81-89.
Csoka et al. "Extracellular ATP protects against sepsis through macrophage P2X7 purinergic receptors by enhancing intracellular bacterial killing" FASEB J 2015 29:3626-3637.
Galbraith et al. "Past, Present, and Future of Augmentation of Monocyte Function in the Surgical Patient" Surg Infect (Larchmt) 2016 17:563-569.
Galbraith et al. "The Significance and Challenges of Monocyte Impairment: for the Ill Patient and the Surgeon" Surg Infect (Larchmt) 2016 17:303-312.
Gordon, J. L. "Extracellular ATP: effects, sources and fate" Biochem J 1986 233:309-319.
Gotts, J. E. and Matthay, M. A. "Sepsis: pathophysiology and clinical management" BMJ 2016 353:1-20.
Gu et al. "Expression of $P2X_7$ purinoceptors on human lymphocytes and monocytes: evidence for nonfunctional $P2X_7$ receptors" Am J Physiol Cell Physiol 2000 279:C1189-1197.
Hotchkiss et al. "Immunosuppression in sepsis: a novel understanding of the disorder and a new therapeutic approach" Lancet Infect Dis 2013 13:260-268.
Hotchkiss, R. S. and Karl, I. E. "The pathophysiology and treatment of sepsis" N Engl J Med 2003 348:138-150.
Idzko et al. "Nucleotide signalling during inflammation" Nature 2014 509:310-317.
Junger, W. G. "Immune cell regulation by autocrine purinergic signaling" Nat Rev Immunol 2011 11:201-212.
Kovach, M. A. and Standiford, T. J. "The function of neutrophils in sepsis" Curr Opin Infect Dis 2012 25:321-327.
Kusner, D. J. and Adams, J. "ATP-induced killing of virulent *Mycobacterium tuberculosis* within human macrophages requires phospholipase D" J Immunol 2000 164:379-388.
La Sala et al. "Alerting and tuning the immune response by extracellular nucleotides" J Leukoc Biol 2003 73:339-343.
Lammas et al. "ATP-induced killing of *Mycobacteria* by human macrophages is mediated by purinergic P2Z(P2X7) receptors" Immunity 1997 7:433-444.
Oberholzer et al. "Interleukin-10: A complex role in the pathogenesis of sepsis syndromes and its potential as an anti-inflammatory drug" Crit Care Med 2002 30:S58-S63.
Pettengill et al. "Reversible inhibition of Chlamydia trachomatis infection in epithelial cells due to stimulation of $P2X_4$ receptors" Infection and Immunity 2012 80:4232-4238.

(Continued)

*Primary Examiner* — Patrick T Lewis
(74) *Attorney, Agent, or Firm* — Licata & Tyrrell P.C.

(57) ABSTRACT

Methods of treating infection including sepsis through modulation of a P2X receptor are provided.

6 Claims, 3 Drawing Sheets

(56) References Cited

PUBLICATIONS

Ralevic, V. and Burnstock, G. "Receptors for purines and pyrimidines" Pharmacol Rev 1998 50:413-492.
Rayah et al. "P2 receptors and immunity" Microbes Infect 2012 14:1254-1262.
Riedemann et al. "The enigma of sepsis" J Clin Invest 2003 112:460-467.
Singer et al. "The Third International Consensus Definitions for Sepsis and Septic Shock (Sepsis-3)" JAMA 2016 315:801-810.
Stearns-Kurosawa et al. "The pathogenesis of sepsis" Annu Rev Pathol 2011 6:19-48.
Torgersen et al. "Macroscopic postmortem findings in 235 surgical intensive care patients with sepsis" Anesth Analg 2009108:1841-1847.
Tracey, K. J. "Understanding immunity requires more than immunology" Nat Immunol 2010 11:561-564.
Ulloa et al. "Scientific and clinical challenges in sepsis" Curr Pharm Des 2009 15:1918-1935.
Van der Poll, T. and Opal, S. M. "Host-pathogen interactions in sepsis" Lancet Infect 2008 8:32-43.
Xiao et al. "A genomic storm in critically injured humans" The Journal of Experimental Medicine 2011 208:2581-2590.

\* cited by examiner

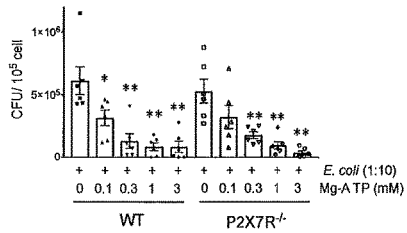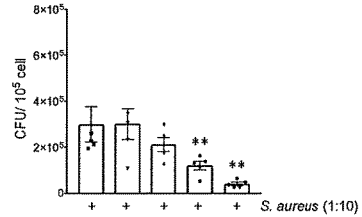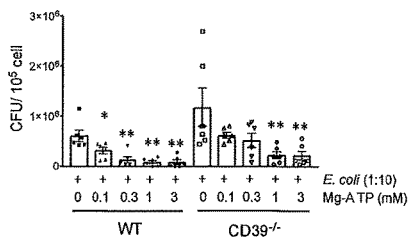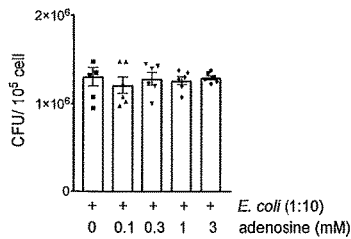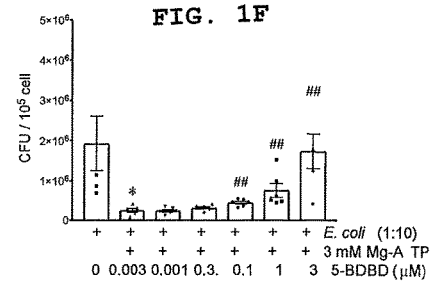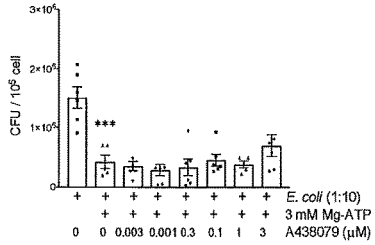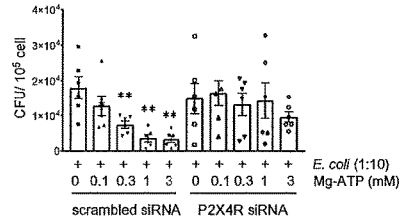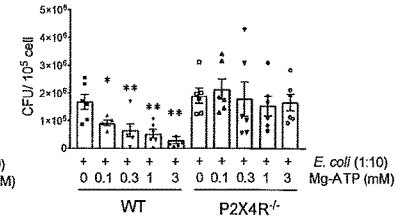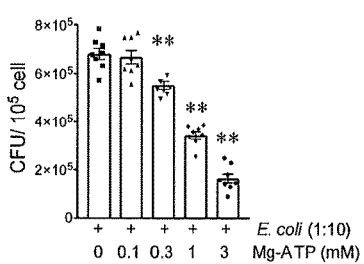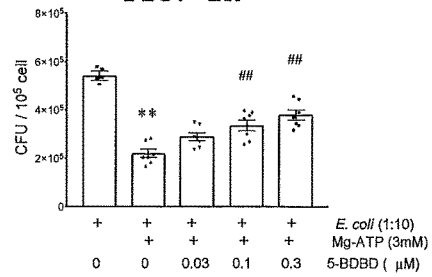

Time (days)

METHODS FOR TREATING INFECTION INCLUDING SEPSIS VIA P2X RECEPTOR MODULATION

This patent application claims the benefit of priority from U.S. Provisional Application Ser. No. 62/532,619, filed Jul. 14, 2017 and U.S. Provisional Application Ser. No. 62/562,770, filed Sep. 25, 2017, the contents of each of which are herein incorporated by reference in their entireties.

This invention was made with Government support under award number R01GM066189 from the National Institutes of Health (NIH). The government has certain rights in the invention.

BACKGROUND

Sepsis and septic shock are related clinical syndromes, where sepsis is defined as life-threatening organ dysfunction caused by a dysregulated host response to infection and septic shock is a subset of sepsis, in which the underlying cellular and metabolic abnormalities are profound enough to increase mortality (Singer et al. *JAMA* 2016 315:801-810). These syndromes are the leading causes of mortality in intensive care units and together are the tenth leading cause of death overall in the United States (Singer et al. JAMA 2016 315:801-810; van der Poll, T. and Opal, S. M. Lancet Infect 2008 8:32-43). It has been estimated that 10 percent of patient with sepsis and 30 percent of patients with septic shock die-far more than the number of U.S. deaths from prostate cancer, breast cancer and AIDS combined ((Singer et al. *JAMA* 2016 315:801-810; Stearns-Kurosawa et al. *Annu Rev Pathol* 2011 6:19-48). Septic patients are generally hospitalized for extended periods, rarely leaving the intensive care unit before 2-3 weeks (Riedemann et al. *J Clin Invest* 2003 112:460-467). Accordingly, sepsis represents a major burden to the US health care system, with costs estimated to be approximately $16.7 billion per year (van der Poll, T. and Opal, S. M. Lancet Infect 2008 8:32-43).

Most commonly, the infection causing sepsis is bacterial. Therefore, the treatment is usually started with IV administration of broad-spectrum antibiotics in an ICU until culture results become available, at which point more narrow-spectrum agents can be used. There is no FDA-approved treatment specifically for sepsis. Most targeted molecular therapies have been unsuccessful in patients. (Jeffrey E Gotts and Michael A Matthay, B M J 2016; 353:bmj.i1585).

Current concepts suggest that an inability to kill invading bacteria or other pathogens effectively due to dysregulation of immunity is a major cause of multiple organ dysfunction syndrome and death in sepsis (Benjamim et al. J Leukoc Biol 2004 75:408-412; Oberholzer et al. Crit Care Med 2002 30:S58-S63. The decreased elimination of bacteria and dysregulation of the immune system lead to systemic inflammatory response syndrome, which contributes to the development of organ failure and shock (Stearns-Kurosawa et al. Annu Rev Pathol 2011 6:19-48; Hotchkiss, R. S. and Karl, I. E. N Engl J Med 2003 348:138-150; Tracey, K. J. Nat Immunol 2010 11: 561-564). Dysregulated host defense and immune response coexisting with increased inflammation also occur in trauma or burn patients that go on to develop the symptoms of sepsis despite an early lack of detection of infectious agent (Xiao et al. The Journal of experimental medicine 2011 208:2581-2590; Ulloa et al. Curr Pharm Des 2009 15:1918-1935). Current treatment options for sepsis are mainly supportive and include the maintenance of systemic perfusion and administration of antibiotics. Despite these interventions, postmortem studies have revealed that the majority of patients still had infectious foci present (Torgersen et al. Anesth Analg 2009 108:1841-1847), thus pointing to a deficit in bacterial clearance.

Macrophages and neutrophils comprise the phagocytic arm of the immune system largely responsible for eradicating bacterial infection. Neutrophil dysfunction and direct neutrophil-mediated organ injury have been proposed to contribute to septic inflammatory organ injury (Kovach, M. A., and Standiford, T. J. Curr Opin Infect Dis 2012 25:321-327). However, impaired cell-autonomous monocyte/macrophage function appears to be primarily responsible for the insufficient anti-bacterial defenses in the septic host (Galbraith et al. Surg Infect (Larchmt) 2016 17, 563-569; Galbraith et al. Surg Infect (Larchmt) 2016 17:303-312; Hotchkiss et al. Lancet Infect Dis 2013 13:260-268).

Intracellular ATP is the universal energy currency of all cells, and is critical for all life from the simplest to the most complex. A plethora of evidence has shown that in response to "stressful" situations, such as infection, trauma, hypoxia, cancer, and metabolic stress, ATP is rapidly released into the extracellular space (Junger, W. G. *Nat Rev Immunol* 2011 11:201-212; Gordon, J. L. Biochem J 1986 233:309-319; la Sala et al. J Leukoc Biol 2003 73:339-343) where ATP exerts mostly immunostimulatory effect (Antonioli et al. Trends Mol Med 2013 19:355-367). ATP acts by binding to specific cell membrane receptors, which are denoted P2 (Burnstock, G. Pharmacological reviews 2006 58:58-86; Rayah et al. Microbes Infect 2012 14: 1254-1262; Idzko et al. Nature 2014 509, 310-317). P2 receptors (P2Rs) fall into two classes, the ionotropic P2X receptors (P2XRs) and the metabotropic P2Y receptors (P2YRs) (Ralevic, V., and Burnstock, G. *Pharmacol Rev* 1998 50:413-492). P2XRs are cell membrane cation channels that are gated by extracellular ATP, and the ATP-mediated opening of these channels allows $Ca^{2+}$ and $Na^+$ influx, and $K^+$ efflux. Seven P2XR subtypes have been cloned (P2X1-7) and ATP activates all P2X subtypes. P2X7Rs, which are expressed at high levels on macrophages, are the best-understood host defense/immune-regulating P2XRs (Gu et al. Am J Physiol Cell Physiol 2000 279:C1189-1197). P2X7R is the sole receptor mediating the effect of extracellular ATP on NLRP3 inflammasome activation and pyroptosis (Rayah et al. Microbes Infect 2012 14: 1254-1262). ATP activation of P2X7Rs also induces the macrophage killing of obligate intracellular bacteria such as *Mycobacterium tuberculosis* and Chlamydiae and obligate intracellular protozoans such as *Trypanosome gondii* and *Leishmania* by macrophages (Lammas et al. Immunity 1997 7:433-444; Kusner, D. J., and Adams, J. J Immunol 2000 164:379-388; Coutinho-Silva et al. Am J Physiol Cell Physiol 2001 280:C81-89). Recently, it was shown that injected ATP augments macrophage-mediated bacterial killing in murine polymicrobial sepsis (Csoka et al. *FASEB J* 2015 29:3626-3637).

Due to the persistent and growing threat of increased antibiotic resistance among pathogenic bacteria, there is an urgent need for treatment methods that do not rely on antibiotic use, such as those methods treating infection that rely on modulating the host immune system rather than targeting the bacterial pathogen. There also exists a need for agents and methods for treating sepsis.

SUMMARY

The inventor has surprisingly discovered that administration of P2X receptors agonists, especially P2X4 agonists, stimulates macrophage responses against pathogens.

Accordingly, an aspect of the present invention relates to methods of treating infection through modulation of a P2X receptor.

In one nonlimiting embodiment, the present invention is directed to a method of treating an infection in a patient in need thereof comprising administering to the patient a therapeutically effective amount of a composition comprising a P2X agonist. In one nonlimiting embodiment, the P2X agonist is a P2X1 agonist. In one nonlimiting embodiment, the P2X agonist is a P2X2 agonist. In one nonlimiting embodiment, the P2X agonist is a P2X3 agonist. In one nonlimiting embodiment, the P2X agonist is a P2X4 agonist. In one nonlimiting embodiment, the P2X agonist is a P2X5 agonist. In one nonlimiting embodiment, the P2X agonist is a P2X6 agonist.

In one nonlimiting embodiment, the infection comprises a bacterial infection. In one nonlimiting embodiment, the bacterial infection is a Gram positive bacterial infection. In one nonlimiting embodiment, the bacterial infection is a Gram negative bacterial infection. In one nonlimiting embodiment, the bacterial infection is an antibiotic-resistant bacterial infection. In one nonlimiting embodiment, the antibiotic-resistant bacterial infection is a multi-drug resistant bacterial infection. In one nonlimiting embodiment, the antibiotic-resistant bacterial infection is an extensively-drug resistant bacterial infection.

In one nonlimiting embodiment, the invention is directed to a method of treating sepsis in a patient in need thereof comprising administering to the patient a therapeutically effective amount of a composition comprising a P2X agonist.

In one nonlimiting embodiment, the P2X agonist comprises a peptide. In one nonlimiting embodiment, the P2X agonist comprises a small molecule. In one nonlimiting embodiment, the P2X agonist comprises a protein. In one nonlimiting embodiment, the P2X agonist comprises an antibody or antigen-binding portion thereof. In one nonlimiting embodiment, the P2X agonist comprises a nucleic acid. In one nonlimiting embodiment, the P2X agonist comprises a fusion protein. In one nonlimiting embodiment, the P2X agonist comprises a ligand. In one nonlimiting embodiment, the P2X agonist comprises a nucleoside triphosphate. In one nonlimiting embodiment, the P2X agonist comprises a nucleoside triphosphate analog. In one nonlimiting embodiment, the P2X agonist comprises adenosine triphosphate (ATP). In one nonlimiting embodiment, the P2X agonist comprises an ATP analog. In one nonlimiting embodiment, the P2X4 agonist comprises ivermectin.

In one nonlimiting embodiment, the P2X agonist is co-administered with at least one additional antibacterial compound. In one nonlimiting embodiment, the at least one additional antibacterial compound comprises an antibiotic. In one nonlimiting embodiment, the administration of the P2X agonist occurs before administration of the at least one additional antibacterial compound. In one nonlimiting embodiment, the administration of the P2X agonist occurs after administration of the at least one additional antibacterial compound. In one nonlimiting embodiment, the administration of the P2X agonist occurs with administration of the at least one additional antibacterial compound.

Another aspect of the present invention relates to a P2X agonist for use in the treatment of an infection in a patient in need thereof. In one nonlimiting embodiment, the P2X agonist is a P2X agonist according to any aspect of the present invention.

Another aspect of the present invention relates to use of a P2X agonist in the manufacture of a medicament for treatment of an infection in a patient in need thereof. In one nonlimiting embodiment, the P2X agonist is a P2X agonist according to any aspect of the present invention.

BRIEF DESCRIPTION OF THE FIGURES

FIGS. 1A through 1K show ATP augments bacterial killing in macrophages in a P2X4R-dependent fashion. FIG. 1A and FIG. 1B show ATP increases intracellular bacterial killing independently of P2X7Rs. Peritoneal macrophages from WT and P2X7R$^{-/-}$ mice were infected with *E. coli* (FIG. 1A) or with *S. aureus* (FIG. 1B) for 90 minutes, which was followed by pulsing the cells with ATP for 5 minutes. Subsequently, after a 2-hour incubation with 400 ng/ml gentamicin, the macrophages were lysed and serial dilutions of their intracellular content were spread onto LB agar plates. *P<0.05; **P<0.01 vs. *E. coli*; n=5-6. FIG. 1C and FIG. 1D show ATP augments bacterial killing independently of adenosine. Macrophages from WT and CD39$^{-/-}$ mice were infected with *E. coli*, pulsed with ATP (FIG. 1C) or adenosine (FIG. 1D), and then incubated with gentamicin for 2 hours, which was followed by intracellular CFU counting. *P<0.05; **P<0.01 vs. *E. coli*; n=4-6. FIG. 1E shows expression of P2Rs in peritoneal macrophages. Peritoneal macrophages were isolated from WT mice and RNA was extracted from untreated cells. RNA was transcribed and quantitative PCRs were conducted. n=6. FIGS. 1F through 1K show P2X4Rs are responsible for the ATP-stimulated increase in bacterial killing in macrophages. Peritoneal macrophages were infected with *E. coli* for 90 min, pretreated with (FIG. 1F) P2X4R antagonist (5-BDBD) or (FIG. 1G) P2X7R antagonist (A438079) for 30 minutes before an ATP pulse for 5 minutes, and then incubated with gentamicin for 2 hours. Killing was determined at the end of this incubation period. *P<0.05; ***P<0.001 vs. *E. coli* treatment; $^{\#\#}$P<0.01 vs. ATP/*E. coli* treatment; n=5-6. In FIG. 1H, macrophages were transfected with scrambled siRNA- or P2X4 siRNA, and the effect of ATP on bacterial killing determined. **P<0.01 vs. *E. coli* treatment; n=6. In FIG. 1I, peritoneal macrophages from WT and P2X4R$^{-/-}$ mice were infected with *E. coli*, pulsed with ATP, incubated with gentamicin for 2 hours and then bacterial killing was determined. **P<0.01 vs. *E. coli* treatment; n=6. In FIGS. 1J and 1K, phorbol 12-myristate 13-acetate (PMA)-differentiated human monocytic THP-1 cells were infected with *E. coli* for 90 minutes, exposed to ATP for 5 minutes and then killing was determined as described above for peritoneal macrophages (FIG. 1J). In other experiments, THP-1 cells were infected with *E. coli*, pretreated with 5-BDBD or vehicle for 30 minutes before a 5-minutes ATP pulse (FIG. 1K), two hours after which intracellular CFUs were determined. **P<0.01; vs. *E. coli* treatment; $^{\#\#}$P<0.01 vs. ATP/*E. coli* treatment. n=6-7. Data are expressed as mean±SEM. All results are representatives of three experiments.

FIG. 2A shows WT mice having improved survival compared to P2X4R$^{-/-}$ mice. Male WT and P2X4R$^{-/-}$ mice were subjected to CLP, and survival was monitored for 7 days. (WT and P2X4R$^{-/-}$; n=24 and 25, respectively). In FIGS. 2D through 2N WT and P2X4R$^{-/-}$ mice were subjected to sham or CLP operation and IL-1β (FIGS. 2D and 2I), IL-6 (FIGS. 2E and 2J), IL-10 (FIGS. 2F and 2K), TNF-α (FIGS. 2G and 2L), and MIP-2 (FIGS. 2H and 2M) levels were determined with ELISAs from blood and peritoneal lavage fluid collected at 16 hours after the operation. In FIG. 2N blood urea nitrogen (BUN) was measured in plasma of sham- or CLP-subjected WT and P2X4R$^{-/-}$ mice 16 hours post-CLP. *P<0.05, P<0.01, and *P<0.001 vs. WT sham and CLP-operated WT; n=3, 4 for sham WT and P2X4R$^{-/-}$; n=6 and 10 for CLP WT and P2X4R$^{-/-}$, respectively. Data are expressed as mean±SEM. All results are representatives of three experiments.

In FIG. 3A ivermectin-treated WT mice showed improved survival compared to vehicle (Veh)-treated WT mice. The survival of ivermectin-treated P2X4R$^{-/-}$ and vehicle-treated P2X4R$^{-/-}$ mice was comparable. WT and P2X4R$^{-/-}$ mice were injected with 10 mg/kg ivermectin or its vehicle and subjected to CLP. The survival of mice was monitored for 7 days *P<0.05-P2X4R$^{-/-}$ injected with vehicle (n=21) vs. WT injected with vehicle (n=25); ***P<0.001—WT injected with ivermectin (n=20); vs. WT injected with vehicle (n=25). In FIGS. 3B and 3C bacterial burden was determined by counting the number of CFUs on blood agar plates after serial dilution of blood and peritoneal lavage samples. Blood and lavage fluid were collected at 16 hours after CLP. *P<0.05 vs. veh (veh and 10 mg/kg ivermectin; n=10 and 9, respectively. In FIG. 3D BUN was determined from plasma of ivermectin- or vehicle-treated mice 16 hours after CLP. *P<0.05. Veh and 10 mg/kg ivermectin; n=10 and 9, respectively. FIGS. 3E and 3F show ivermectin increasing intracellular killing of *E. coli* in cultured macrophages. Peritoneal macrophages were infected with *E. coli* for 90 minutes and then pulsed with ATP for 5 minutes. ATP was then removed and the macrophages were incubated with ivermectin for 30 minutes. Thereafter the ivermectin was removed and the cells were incubated in medium containing gentamicin for another 2 hours. The cells were then lysed and serial dilutions of intracellular content were spread onto LB agar plates. *P<0.05 (n=5-6); **P<0.01 (n=5-6). Data are expressed as mean±SEM. All results are representatives of three experiments.

DETAILED DESCRIPTION

Figure 2A:
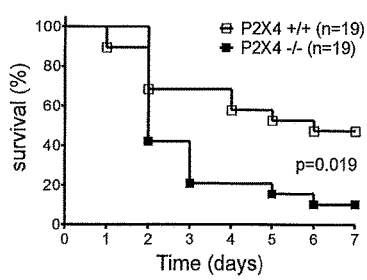
FIGS. 2A through 2N show P2X4Rs decrease mortality, bacterial load, inflammatory cytokines and chemokines, and organ injury in sepsis.

The following non-limiting definitions are provided to aid in the understanding of the invention:

As used herein and in the appended claims, the singular forms "a," "and" and "the" include plural references unless the context clearly dictates otherwise. The term "(s)" following a noun contemplates the singular or plural form, or both.

The term "and/or" means any one of the items, any combination of the items, or all of the items with which this term is associated.

The phrases "in one nonlimiting embodiment," "in various nonlimiting embodiments," "in some nonlimiting embodiments," and the like are repeatedly used. Such phrases do not necessarily refer to the same embodiment, but they may unless the context dictates otherwise.

The terms "comprising," "having," and "including" are synonymous, unless the context dictates otherwise.

As used herein, the term "treating" or "treatment" of a disease may refer to executing a protocol, which may include administering one or more drugs to a patient (human or otherwise), to alleviate signs or symptoms of the disease. Thus, in the case of treating an infection, including a bacterial infection, "treating" or "treatment" may arise in a situation where a course of treatment is advanced to reduce infection in a patient as measured by, e.g., a reduction in total pathogenic load.

As used herein, the term "carriers" may include pharmaceutically acceptable carriers, excipients, or stabilizers that are nontoxic to the cell or mammal being exposed thereto at the dosages and concentrations employed. Often the pharmaceutically acceptable carrier is an aqueous pH buffered solution. Examples of physiologically acceptable carriers include, but not limited to, buffers such as phosphate, citrate, and other organic acids; antioxidants including, but not limited to, ascorbic acid; low molecular weight (less than about 10 residues) polypeptide; proteins, such as, but not limited to, serum albumin, gelatin, or immunoglobulins; hydrophilic polymers such as, but not limited to, polyvinylpyrrolidone; amino acids such as, but not limited to, glycine, glutamine, asparagine, arginine or lysine; monosaccharides, disaccharides, and other carbohydrates including, but not limited to, glucose, mannose, or dextrins; chelating agents such as, but not limited to, EDTA; sugar alcohols such as, but not limited to, mannitol or sorbitol; salt-forming counterions such as, but not limited to, sodium; and/or nonionic surfactants such as, but not limited to, TWEEN.; polyethylene glycol (PEG), and PLURONICS. Any combination of such components, including the probable inclusion of a bacteriostat, may be useful to fill the formulations of the present invention.

The terms "co-administration," "co-administered," and "in combination with" as used herein may refer to the administration of at least two agents or therapies to a subject. In some embodiments, the co-administration of two or more agents/therapies is concurrent. In other embodiments, a first agent/therapy is administered before a second agent/therapy. Those of skill in the art understand that the formulations and/or routes of administration of the various agents/therapies used may vary.

As used herein, the term "patient" may refer to a biological system to which a treatment can be administered. A biological system can include, for example, an individual cell, a set of cells (e.g., a cell culture), an organ, a tissue, or a multi-cellular organism. A "patient" can refer to a human patient or a non-human patient.

Where a value of ranges is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference in their entireties.

The term "about" refers to a range of values which would not be considered by a person of ordinary skill in the art as substantially different from the baseline values. For example, the term "about" may refer to a value that is within 20%, 15%, 10%, 9%, 8%, 7%, 6%, 5%, 4%, 3%, 2%, 1%, 0.5%, 0.1%, 0.05%, or 0.01% of the stated value, as well as values intervening such stated values.

Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates which may need to be independently confirmed.

Each of the applications and patents cited in this text, as well as each document or reference, patent or non-patent literature, cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference in their entirety. More generally, documents or references are cited in this text, either in a Reference List before the claims; or in the text itself; and, each of these documents or references ("herein-cited references"), as well as each document or reference cited in each of the herein-cited references (including any manufacturer's specifications, instructions, etc.), is hereby expressly incorporated herein by reference.

The following detailed description is merely illustrative in nature and is not intended to limit the embodiments of the subject matter or the application and uses of such embodiments. Furthermore, there is no intention to be bound by any expressed or implied theory presented in the preceding technical field, background, summary or the following detailed description.

The present invention generally relates to methods of treating infection through modulation of P2X receptors. In one nonlimiting embodiment, the invention is directed to a method of treating sepsis in a patient in need thereof through modulation of P2X receptors.

P2X receptors belong to a class of receptors known as purinergic receptors. Purinergic receptors (also known as purinoceptors) comprise a family of plasma membrane molecules found ubiquitously throughout mammalian tissues. Purinergic receptors come in two main varieties, P1 receptors and P2 receptors. P2 receptors are further classified into five different subclasses, P2X, P2Y, P2Z, P2U, and P2T. P2Y, P2U, and P2T are known as metabotropic receptors, whereas P2X and P2Z are known as tonotropic receptors. P1 receptors are activated by adenosine, whereas P2Y receptors are activated by nucleotides. P2X receptors are activated by ATP, and are ligand-gated ion channels, as opposed to P1 and P2Y receptors which are G protein-coupled receptors.

P2X receptor subtypes include P2X1, P2X2, P2X3, P2X4, P2X5, P2X6, and P2X7. Of particular interest is P2X4, as shown in Example 1. Each P2X receptor subtype shares common topology, having two domains that span the plasma membrane, an extracellular loop and intracellular carboxyl and amino terminus. The amino terminus has a consensus site for protein kinase C phosphorylation. P2X receptors, including P2X4, generally require at least 3 ATP molecules to activate. However, P2X4 is subject to modulation by changes in the extracellular environment. For example, in an in acidic environment (pH<7), the sensitivity of P2X4 to ATP is lessened. In contrast, certain compositions, such as metals, e.g. zinc, may potentiate ATP-gated currents through P2X4. Without wishing to be bound by theory, such allosteric modulation of P2X receptors by pH and metal may be conferred by the presence of basic side chains, e.g. histidine side chains, in the extracellular domains of the P2X receptors. Accordingly, in some embodiments, the method comprises co-administration of zinc alongside a P2X agonist.

P2X4 receptors in particular are also sensitive to modulation by ivermectin (22,23-dihydroavermectin), a macrocyclic lactone. Without wishing to be bound by theory, ivermectin is believed to potentiate ATP-gated currents through P2X4 receptors by increasing open probability of the channel in the presence of ATP by interacting with the transmembrane (TM) domains within the plasma membrane (Priel A. and Silberberg S. D. J. Gen. Physiol. 2004 123 (3): 281-93). Accordingly, in some nonlimiting embodiments, the method comprises co-administration of ivermectin alongside a P2X agonist.

P2X receptors are involved in a diverse number of physiological roles that reflect the diversity within the subtypes of the P2X receptors. For example, P2X receptors are involved in modulation of vascular tone, cardiac rhythm/contractibility, chronic pain/nociception, and neuronal-glial integration. P2X7 has been previously reported as involved in stimulating the role of P2 macrophage function (Wewers, M. D. and Sarkar, A. Purinergic Signalling 2009 5 2:189-195). Accordingly, in some nonlimiting embodiments, the method comprises treating an infection in a patient in need thereof comprising administering to said patient a therapeutically effective amount of a composition comprising a P2X agonist. Of particular interest is the P2X4 receptor and P2X4 agonists.

The inventors herein have surprisingly discovered that administration of a P2X4 agonist, e.g. ATP, increases stimulates macrophage responses against pathogens, rendering P2X4 agonists particularly useful in treating infection, particularly bacterial infections. The pathogens may be any pathogenic organisms, including fungal, bacterial, protozoan, or similar organisms. Of particular interest are bacterial organisms. The bacterial organisms may be either Gram-positive or Gram-negative bacterial organisms. The present invention may be particularly useful against combating antibiotic resistance since the mechanism of action does not rely on administration of antibiotics, although as discussed infra the P2X agonists of the present invention, including P2X4 agonists, may be co-administered with one or more antibacterial compositions (e.g. antibiotics). Accordingly, the bacterial organisms may be, but are not necessarily, drug-resistant bacteria, multi-drug resistant (MDR) bacteria, or extensively drug resistant (XDR) bacteria.

Particular bacteria of interest may include, but are not limited to, human pathogens such as those found within the genus *Bacillus, Bartonella, Bordetella, Borrelia, Brucella, Campylobacter, Chlamydia, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Staphylococcus, Streptococcus, Treponema, Ureaplasma, Vibrio,* and *Yessinia*. Particular species of interest may include, but are not limited to, human pathogens such as *Bacillus anthracis, Bacillus cereus, Bartonella henselae, Bartonella quintana, Bordetella pertussis, Borrelia burgdorferi, Borrelia garinii, Borrelia afzelii, Borrelia recurrentis, Brucella abortus, Brucella canis, Brucella melitensis, Bru-* cella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheria, Enterococcus faecalis, Enterococcus faecium, Escherichia coli, Francisella tularensis, Haemophilus influenzae, Helicobacter pylori, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumoniae, Neisseria gonorrhoeae, Neisseria meningitides, Pseudomonas aeruginosa, Rickettsia, Salmonella typhi, Salmonella typhimurium, Shigella sonnet, Staphylococcus aureus, Staphylococcus epidermidis, Staphylococcus saprophyticus, Streptococcus agalactiae, Streptococcus pneumoniae, Streptococcus pyogenes, Treponema pallidum, Ureaplasma urealyticum, Vibrio cholera, Yersinia pestis, Yersinia enterocolitica* and *Yersinia pseudotuberculosis.*

In one nonlimiting embodiment, the invention is directed to a method of treating sepsis in a patient in need thereof comprising administering to the patient a therapeutically effective amount of a composition comprising a P2X agonist.

The P2X agonists may also be co-administered with other antibacterial compounds, e.g. traditional antibiotics. This may lead to synergistic results that go beyond the additive results of administering just the P2X agonists or just the antibacterial compounds alone. The antibiotic can be any of the following: Amikacin, Gentamicin, Kanamycin, Neomycin, Netilmicin, Tobramycin, Paromomycin, Streptomycin, Spectinomycin, Gedlanamycin, Herbimycin, Rifaximin, Loracarbef, Ertapenem, Doripenem, Imipenem, Cilastatin, Meropenem, Cefadroxil, Cefazolin, Cefalotin, Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline fosamil, Ceftobiprole, Teicoplanin, Vancomycin, Telavancin, Dalbavancin, Ortiavancin, Clindamycin, Lincomycin, Daptomycin, Azithromycin, Clarithromycin, Dirithromycin, Erythromycin, Roxithromycin, Troleandomycin, Telithromycin, Spiramycin, Aztreonam, Furazolidone, Nitrofurantoin, Linezolid, Posizolid, Radezolid, Torezolid, Amoxocillin, Ampicillin, Azlocillin, Carbenicillin, Cloxacillin, Dicloxacillin, Flucloxacillin, Mezlocillin, Methicilin, Nafcillin, Oxacillin, Penicillin, Piperacillin, Temocillin, Ticarcillin, Bactricin, Colistin, Polymixin B, Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfacetamide, Sulfadiazine, Sulfadimethoxine, Sulfamethizole, Sulfamethoxazole, Sulfanilimide, Sulfasalazine, Sulfisoxazole, Trimethoprim-Sulfamethoxasole, Sulfonamidochrysoidine, Demeclocycline, Doxycyline, Minocycline, Oxytetracycline, Clofazimine, Dapsone, Capreomycin, Cycloserine, Ethambutol, Ethionamide, Isoiazid, Pyrazinamide, Rifampicin, Rifabutin, Rifapentine, Streptomycin, Araphenamine, Chloramphenicol, Fosfomycin, Fusidic acid, Metronidazole, Mupricoin, Platensimycin, Quinupristin, Dalfopristin, Thiamphenicol, Tigecycline, Tinidazole, Trimethoprim, and combinations thereof.

The P2X receptor agonists may be any compound that stimulates P2X signaling. Of particular interest are those compounds which stimulate P2X4 signaling. The P2X receptor agonists, including but not limited to P2X4 agonists, may include but are not limited to peptides, small molecules, proteins, nucleic acids, and antibodies, i.e. agonistic-antibodies. P2X4 agonists in particular may include ATP or ATP analogs. As shown in Example 1 infra, administration of P2X4 agonists (including ATP) stimulates macrophage response against pathogenic bacteria in vitro. One of ordinary skill in the art will appreciate the link between in vitro studies and in vivo therapeutic efficacy of such P2X4 agonists. In one nonlimiting embodiment, the P2X4 agonist comprises ivermectin.

Administration of the P2X receptor agonists may be by any means known in the art, including oral, parental, rectal, topical, intradermal, intramuscular, intravenous, or by continuous means such as a drip or an infusion pump, or by an implant, e.g. such as a medical device or implant coated with a composition comprising the P2X receptor agonists. The amount and frequency for which the P2X receptor agonists will be administered depends on the particular condition which is being treated, as well as the patient's individual history and other such related circumstances. Determining such dosing parameters are within the skill of a physician.

The role of P2X7Rs in mediating the ATP-induced increase of *E. coli* killing was examined. Unexpectedly, the inventors herein found that the ATP-stimulated killing of *E. coli* was independent of P2X7Rs, as ATP increased killing of *E. coli* both in WT and P2X7R$^{-/-}$ macrophages (FIG. 1A). This observation raised two possibilities. The first possibility was that ATP killed E. coif not through a direct effect on P2Rs but indirectly by being degraded to adenosine, which also has wide-ranging effects on macrophages via adenosine/P1 receptors. However, the ATP-stimulated bacterial killing was not mediated by the degradation of ATP to adenosine, as ATP also killed *E. coli* in macrophages lacking CD39 (CD39$^{-/-}$) (FIG. 10), which initiates ATP degradation to adenosine. In addition, adenosine itself failed to increase *E. coli* killing (FIG. 1D). The second possibility was that ATP killed bacteria through another macrophage P2R. To identify this P2R, studies were performed to identify which P2Rs were expressed in peritoneal macrophages. Quantitative PCR data showed that peritoneal macrophages expressed several P2Rs, and P2X4Rs were the most abundant (FIG. 1E). Thus, the role of P2X4Rs was investigated further. Using a pharmacological approach, it was observed that a selective P2X4R antagonist (FIG. 1F), but not P2X7R antagonist (FIG. 1G) prevented the stimulatory effect of ATP on *E. coli* killing. In addition, shRNA-mediated silencing of P2X4Rs largely reversed the stimulatory effect of ATP on *E. coli* killing (FIG. 1H). Finally, it was demonstrated that in macrophages isolated from P2X4R$^{-/-}$ mice, ATP failed to stimulate *E. coli* killing, whereas in macrophages from WT littermate controls ATP caused a dose-dependent increase in killing (FIG. 1I). The stimulatory role of P2X4Rs was also confirmed in regulating bacterial killing in human macrophages, as ATP increased killing of *E. coli* and a P2X4R antagonist inhibited the stimulatory effect of ATP on *E. coli* killing in phorbol 12-myristate 13-acetate (PMA)-differentiated human monocytic THP-1 cells (FIGS. 1J and 1K). These data indicate that P2X4Rs mediate the stimulatory effect of ATP bacterial killing in macrophages.

Figure 2B:
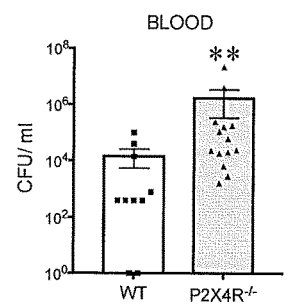
In FIGS. 2B and 2C bacterial burden was determined by counting the number of CFUs on blood agar plates after serial dilution of blood and peritoneal lavage samples. Blood and lavage fluid were collected at 16 hour after CLP. **P<0.01 vs. WT (WT and P2X4R$^{-/-}$; n=10 and 14, respectively, for blood; n=10 and 14, respectively, for lavage).
Figure 2C:
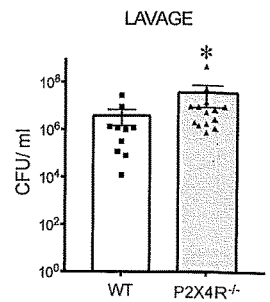
Figure 2D:
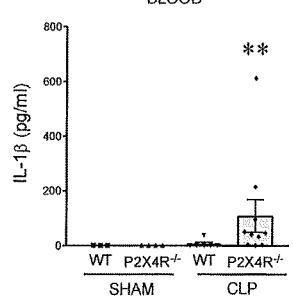
Figure 2E:
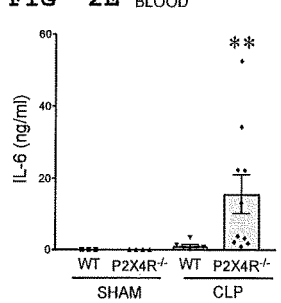
Figure 2F:
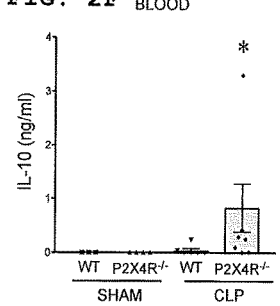
Figure 2G:
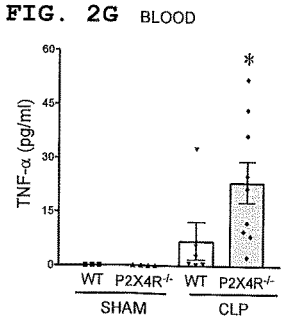
Figure 2H:
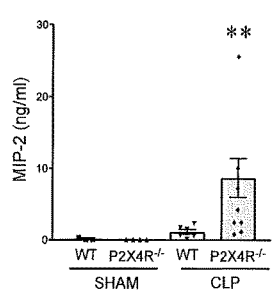
Figure 2I:
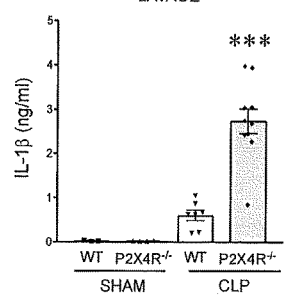
Figure 2J:
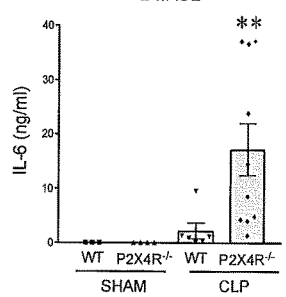
Figure 2K:
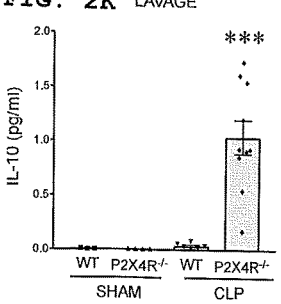
Figure 2L:
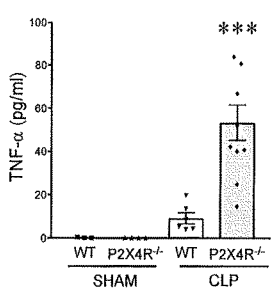
Figure 2M:
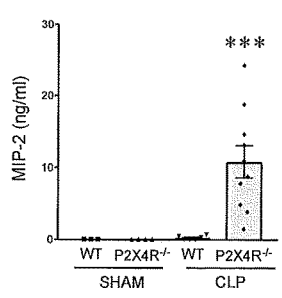
Figure 2N:
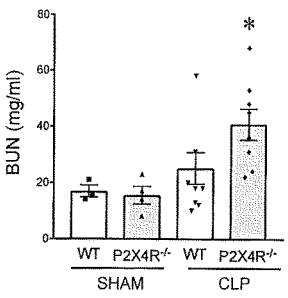

The role of P2X4Rs in regulating the host's response to bacterial infection in vivo was also examined. WT and P2X4R$^{-/-}$ mice were subjected to sepsis by cecal ligation and puncture (CLP) and their survival was monitored. It was observed that the survival rate of WT mice was higher than that of the P2X4R$^{-/-}$ animals, indicating that P2X4Rs are protective against bacterial infection in vivo (FIG. 2A). The host's immune response was assessed at 16 hours after the CLP procedure, at which time bacterial dissemination and inflammation are at their maximum. It was found that WT mice exhibited decreased bacterial burden in both the blood and peritoneal cavity compared to P2X4R$^{-/-}$ mice (FIGS. 2B and 2C), indicating that P2X4Rs control bacterial burden. The inflammatory status of the mice was also investigated by measuring levels of inflammatory cytokines and chemokines. It was found that P2X4R$^{-/-}$ mice had higher levels of inflammatory cytokines and chemokines in blood and peritoneum compared to WT mice (FIG. 2D-M). Organ injury was also assessed to better understand the role of P2X4Rs in regulating host pathophysiology. Septic P2X4R$^{-/-}$ mice exhibited increased kidney injury as indicated by increases in plasma blood urea nitrogen (BUN) levels (FIG. 2N).

Figure 3A:
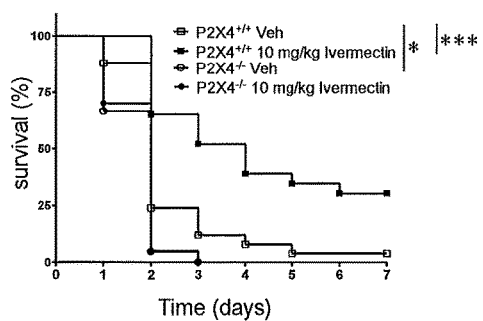
FIGS. 3A through 3F shows ivermectin, an allosteric activator of P2X4Rs improves survival, and decreases bacterial burden and organ injury in mice after sepsis, and augments bacterial killing by macrophages.
Figure 3B:
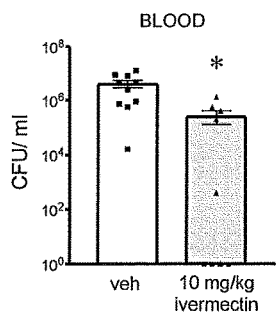
Figure 3C:
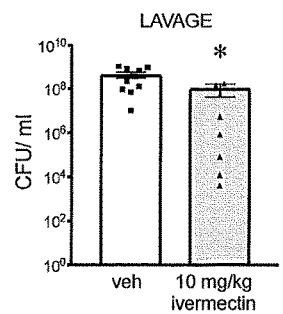
Figure 3D:
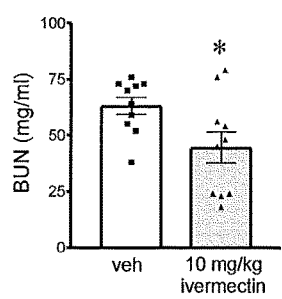
Figure 3E:
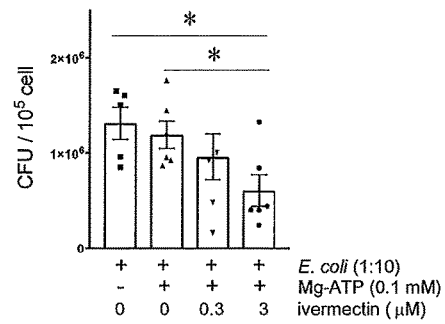
Figure 3F:
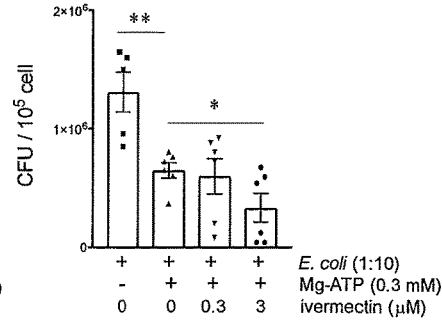

From these studies, it was believed that pharmacological activation of P2X4Rs would have an effect opposite to that of inactivating these receptors genetically; that is that the pharmacological activation of P2X4Rs would be protective. To examine this, mice were injected with ivermectin, an anti-helminth drug that is a partial allosteric activator of P2X4Rs (Khakh et al. J Neurosci 1999 19:7289-7299) 90 minutes after performing CLP. Ivermectin improved survival (FIG. 3A), which occurred in a P2X4R-dependent manner, as ivermectin failed to improve survival in P2X4R$^{-/-}$ mice. Ivermectin also decreased bacteria (FIGS. 3B and C), and diminished plasma BUN levels (FIG. 3D). Furthermore, ivermectin potentiated the ATP stimulation of bacterial killing in macrophages in vitro (FIGS. 3E and 3F).

These data confirm the antibacterial and organ protective effects of P2X4Rs and the usefulness of P2X agonists in infection and sepsis.

The following non-limiting examples serve to further illustrate the present invention.

EXAMPLES

Example 1

ATP Induces Bacterial Killing by Macrophages, Mediated by P2X4 Receptors

Naive, thioglycollate-elicited murine peritoneal macrophages were treated with *E. coli* (K-12 strain) at 1:15 cell:bacteria ratio in vitro and incubated for 90 minutes to allow for phagocytosis to occur. After 90 minutes, the cells were washed to remove non-phagocytosed bacteria and treated with increasing concentrations (0.1 to 3 μM) of ATP or adenosine for 5 minutes. After 5 minutes, the medium was removed and the cells were washed extensively.

New medium was added that was supplemented with 100 μg/mL gentamicin. This allowed the maturation of the phagosome and killing of the phagocytosed bacteria. The cells were incubated for approximately 2 hours at 37° C. After incubation, the cells were washed 5 times to remove the gentamicin and were lysed. Colony forming units (CPUs) were determined after an overnight incubation on agar.

Example 2

CLP Model

Male C57B16/J rmce were anesthetized using Nembutal, and a 2-cm midline laparotomy was performed to allow exposure of the cecum with adjoining intestine. Approximately two-thirds of the cecum was tightly ligated with a 3.0 silk suture, and the ligated part of the cecum was perforated twice (through and through) with a 20-gauge needle. The cecum was then gently squeezed to extrude a small amount of feces from the perforation sites. The cecum was then returned to the peritoneal cavity, and the laparotomy closed in two layers with 4.0 silk sutures. Sham-operated animals underwent the same procedure without ligation or puncture of the cecum. The mice were resuscitated with 1 ml of physiological saline injected subcutaneously and returned to their cages with free access to food and water, and survival was monitored for 7 days (p<0.05). Survival curves were analyzed using two-tailed Fisher's exact test.

Example 3

Measurement of Bacterial Load (CFU)

Bacterial load in mice subjected to CLP was measured at 16 h after surgery. Dilutions of blood or peritoneal lavage fluid were cultured on tryptose blood agar plates, and the number of bacterial colonies was counted. CFU results are representative of 3 separate experiments. Data are the mean±SEM of n=6-9 mice per group. *p<0.05. Two-tailed t testing was used to compare CPUs. Statistical significance was assigned top values smaller than 0.05.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. A method of treating a bacterial infection in a patient in need thereof comprising administering to said patient a therapeutically effective amount of a composition comprising a P2X4 specific agonist, wherein said bacterial infection is from a genus selected from *Bacillus, Bartonella, Bordetella, Borrelia, Brucella, Campylobacter, Clostridium, Corynebacterium, Enterococcus, Francisella, Haemophilus, Helicobacter, Legionella, Leptospira, Listeria, Mycobacterium, Mycoplasma, Neisseria, Pseudomonas, Rickettsia, Salmonella, Staphylococcus, Streptococcus, Treponema, Ureaplasma, Vibrio*, and *Yessinia*.

2. The method of claim 1 wherein the P2X4 specific agonist is selected from the group consisting of peptides, small molecules, proteins, nucleic acids, and antibodies.

3. The method of claim 1 wherein the bacterial infection is an antibiotic-resistant bacterial infection.

4. The method of claim 1 wherein the composition further comprises a pharmaceutically acceptable carrier.

5. The method of claim 1 wherein the patient is suffering from sepsis.

6. The method of claim 1 wherein the P2X4 agonist comprises ivermectin.

* * * * *